(12) United States Patent
Maeda

(10) Patent No.: US 10,878,571 B2
(45) Date of Patent: Dec. 29, 2020

(54) IMAGING APPARATUS AND IMAGING METHOD FOR IMAGING BIOLOGICAL SAMPLES IN A TIME-SERIES ORDER

(71) Applicant: FUJIFILM Corporation, Tokyo (JP)

(72) Inventor: Kiyohiro Maeda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 170 days.

(21) Appl. No.: 16/176,637

(22) Filed: Oct. 31, 2018

(65) Prior Publication Data

US 2019/0066299 A1 Feb. 28, 2019

Related U.S. Application Data

(63) Continuation of application No. PCT/JP2017/015865, filed on Apr. 20, 2017.

(30) Foreign Application Priority Data

May 18, 2016 (JP) .................................. 2016-099395

(51) Int. Cl.
*G06T 7/00* (2017.01)
*C12Q 1/02* (2006.01)
(Continued)

(52) U.S. Cl.
CPC ............. *G06T 7/0016* (2013.01); *C12M 1/34* (2013.01); *C12Q 1/02* (2013.01); *C12Q 1/025* (2013.01);
(Continued)

(58) Field of Classification Search
CPC ........ G06T 7/0016; C12Q 1/02; G01N 21/17; G01N 33/4833; G01N 35/00584;
(Continued)

(56) References Cited

U.S. PATENT DOCUMENTS

| | | |
|---|---|---|
| 2004/0034242 A1 | 2/2004 | Yang |
| 2014/0106389 A1 | 4/2014 | Loewke et al. |
| 2017/0073630 A1 | 3/2017 | Matsubara |

FOREIGN PATENT DOCUMENTS

| | | |
|---|---|---|
| JP | 2003-523975 A | 8/2003 |
| JP | 2009-232710 A | 10/2009 |

(Continued)

OTHER PUBLICATIONS

Lit-Hsin Loo et al., "Image-based multivariate profiling of drug responses from single cells", Nature Methods, vol. 4 No. 5, Apr. 1, 2007, 9 pages total.

(Continued)

*Primary Examiner* — Siamak Harandi
(74) *Attorney, Agent, or Firm* — Sughrue Mion, PLLC

(57) ABSTRACT

An imaging apparatus includes an imaging unit that images, in a time series order, each of a first biological sample having undergone a first process and a second biological sample which has undergone a second process and is of the same type as the type of the first biological sample, and an imaging interval setting portion that acquires a first image obtained by imaging the first biological sample, and a second image obtained by imaging the second biological sample at the same timing as a timing of the first biological sample, and sets an imaging interval of the first and the second biological sample on the basis of a difference between feature data of the first image and feature data of the second image or a change amount of the difference, in which the imaging unit images the first and the second biological sample by using the imaging interval.

20 Claims, 4 Drawing Sheets

(51) Int. Cl.
| | |
|---|---|
| *G01N 33/483* | (2006.01) |
| *G01N 21/17* | (2006.01) |
| *C12M 1/34* | (2006.01) |
| *G01N 35/00* | (2006.01) |
| *G01N 33/50* | (2006.01) |
| *G01N 15/02* | (2006.01) |
| *G02B 21/36* | (2006.01) |
| *G01N 15/14* | (2006.01) |
| *G06T 1/00* | (2006.01) |
| *G06T 7/62* | (2017.01) |
| *G06T 7/11* | (2017.01) |
| *G06T 7/174* | (2017.01) |
| *H04N 5/232* | (2006.01) |
| *G01N 15/10* | (2006.01) |
| *G03B 15/00* | (2006.01) |

(52) U.S. Cl.
CPC ..... *G01N 15/0227* (2013.01); *G01N 15/1475* (2013.01); *G01N 21/17* (2013.01); *G01N 33/483* (2013.01); *G01N 33/4833* (2013.01); *G01N 33/5008* (2013.01); *G01N 35/00584* (2013.01); *G02B 21/365* (2013.01); *G06T 1/00* (2013.01); *G06T 7/11* (2017.01); *G06T 7/174* (2017.01); *G06T 7/62* (2017.01); *H04N 5/23222* (2013.01); *G01N 2015/1006* (2013.01); *G01N 2015/1486* (2013.01); *G01N 2015/1493* (2013.01); *G01N 2015/1497* (2013.01); *G03B 15/00* (2013.01); *G06T 2207/10056* (2013.01); *G06T 2207/20224* (2013.01); *G06T 2207/30024* (2013.01); *G06T 2207/30242* (2013.01)

(58) Field of Classification Search
CPC ........... G01N 33/5008; G01N 15/0227; G01N 15/1475; C12M 1/34; G02B 21/365
See application file for complete search history.

(56) References Cited

FOREIGN PATENT DOCUMENTS

| | | | |
|---|---|---|---|
| JP | 2012-095627 A | | 5/2012 |
| JP | 2014-504849 A | | 2/2014 |
| JP | 2015-223174 | * | 5/2014 |
| JP | 2015-086186 A | | 5/2015 |
| JP | 2015-223174 A | | 12/2015 |
| JP | 2016-069348 A | | 5/2016 |

OTHER PUBLICATIONS

Extended European Search Report dated Apr. 18, 2019 issued by the European Patent Office in counterpart application No. 17799109.8.
Communication dated May 7, 2019 issued by the Japanese Patent Office in counterpart application No. 2016-099395.
International Search Report of PCT/JP2017/015865 dated Jul. 25, 2017 [PCT/ISA/210].
Written Opinion dated Jul. 25, 2017, issued by the International Searching Authority in application No. PCT/JP2017/015865 [PCT/ISA/237].
International Preliminary Report on Patentability with Translation of Written Opinion dated Nov. 20, 2018, issued by the International Searching Authority in application No. PCT/JP2017/015865.

* cited by examiner

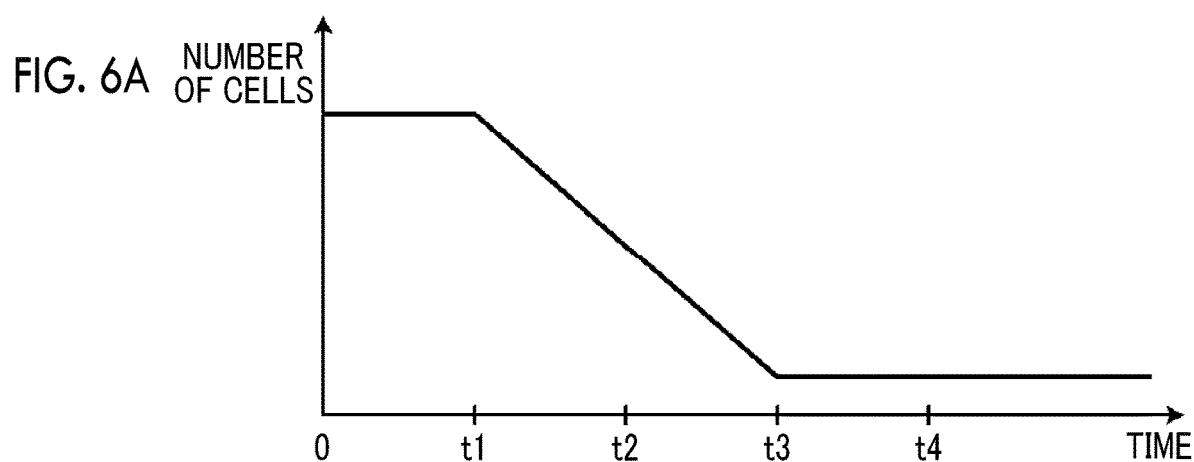
FIG. 6A
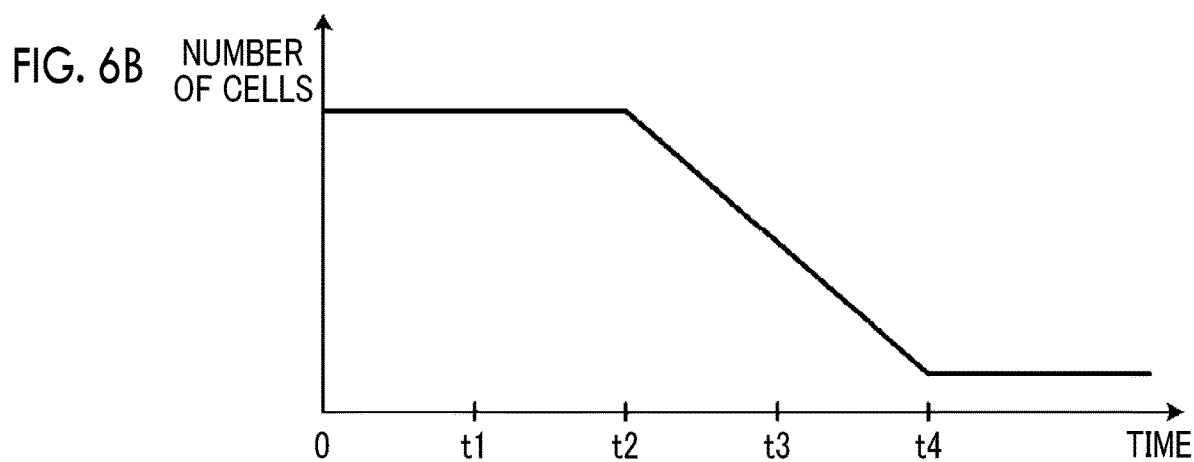
FIG. 6B
FIG. 7
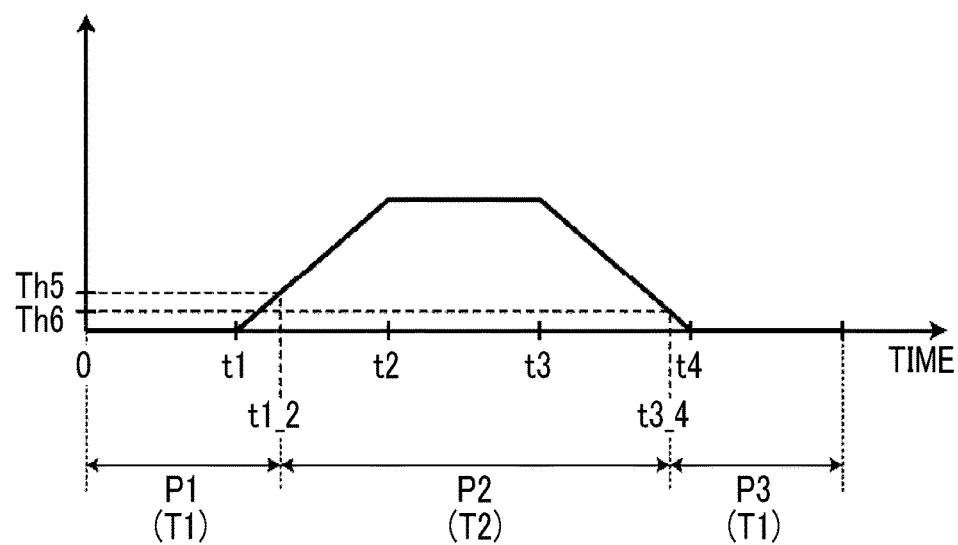

IMAGING APPARATUS AND IMAGING METHOD FOR IMAGING BIOLOGICAL SAMPLES IN A TIME-SERIES ORDER

CROSS-REFERENCE TO RELATED APPLICATIONS

This application is a Continuation of PCT International Application No. PCT/JP2017/015865 filed on Apr. 20, 2017, which claims priority under 35 U.S.C § 119(a) to Japanese Patent Application No. 2016-099395 filed on May 18, 2016. Each of the above application(s) is hereby expressly incorporated by reference, in its entirety, into the present application.

BACKGROUND OF THE INVENTION

1. Field of the Invention

The present invention relates to an imaging apparatus and an imaging method capable of imaging biological samples in a time-series order.

2. Description of the Related Art

In the related art, in research and development and product manufacturing processes in drug discovery and regenerative medical fields, temporal imaging of biological samples are commonly used. For example, in order to evaluate an effect which a compound has on a cell, changes of a phenotype after the compound is provided to the cell are imaged over time with a microscope. This imaging is often manually performed, but may be automatically performed in order to reduce human cost.

For example, JP2014-504849A has proposed an apparatus which automatically temporally images a biological sample.

SUMMARY OF THE INVENTION

Here, regarding one of tasks in an apparatus performing automatic temporal imaging, there is adjustment of an imaging interval. In a case where an imaging interval is long, there is high concern of failing to recognize changes of a biological sample. On the other hand, in a case where an imaging interval is short, there is less concern of failing to recognize changes of a biological sample, but there is a problem in that acquired image data is redundant.

Therefore, JP2014-504849A has proposed a method of changing an imaging interval on the basis of a result of analyzing a captured image of the biological sample in real time.

However, in the method disclosed in JP2014-504849A, since a living body is inherently unstable due to an environment in which the biological sample is placed, there is a probability that an imaging interval may be determined as being changed when the imaging interval is not originally required to be changed, or a probability that the imaging interval may fail to be changed when the imaging interval is originally required to be changed. There is a probability that an imaging interval may be determined as being required to be shortened in a situation in which the imaging interval is originally required to be lengthened, or a probability that an imaging interval may be determined as being required to be lengthened in a situation in which the imaging interval is originally required to be shortened, and thus it is difficult to realize practical automatic adjustment.

In light of the above-described problems, an object of the present invention is to provide an imaging apparatus and an imaging method capable of appropriately setting an imaging interval of a biological sample without being influenced by an environment in which the biological sample is placed or the like, and thus capturing an image in which a temporal change of a state of the biological sample is checked in more detail without performing wasteful imaging.

According to an aspect of the present invention, there is provided an imaging apparatus comprising an imaging unit that images, in a time series order, each of a first biological sample having undergone a first process and a second biological sample which has undergone a second process which is a comparison target with the first process, is different from the first process and is of the same type as the type of the first biological sample; and an imaging interval setting portion that acquires a first image obtained by imaging the first image, and a second image obtained by imaging the second biological sample at the same timing as a timing of the first biological sample, and sets an imaging interval of the first biological sample and the second biological sample on the basis of a difference between feature data of the first image and feature data of the second image or a change amount of the difference, in which the imaging unit images the first biological sample and the second biological sample by using the imaging interval set by the imaging interval setting portion.

In the imaging apparatus according to the aspect of the present invention, the imaging interval setting portion may set an imaging interval after an imaging time point of the first image and the second image to be shorter than an imaging interval related to the imaging time point in a case where a difference between the feature data of the first image and the feature data of the second image or a change amount of the difference is equal to or more than a preset first threshold value.

In the imaging apparatus according to the aspect of the present invention, the imaging interval setting portion may set an imaging interval after an imaging time point of the first image and the second image to be longer than an imaging interval related to the imaging time point in a case where a difference between the feature data of the first image and the feature data of the second image or a change amount of the difference is equal to or less than a preset second threshold value.

In the imaging apparatus according to the aspect of the present invention, the imaging interval setting portion may set the imaging interval to become shorter as a difference between the feature data of the first image and the feature data of the second image or a change amount of the difference becomes larger.

In the imaging apparatus according to the aspect of the present invention, the imaging interval setting portion may set the imaging interval to become longer as a difference between the feature data of the first image and the feature data of the second image or a change amount of the difference becomes smaller.

In the imaging apparatus according to the aspect of the present invention, cells may be used as the first biological sample and the second biological sample.

In the imaging apparatus according to the aspect of the present invention, the imaging interval setting portion may acquire, as the feature data, the number of cells included in each of the first biological sample and the second biological sample.

In the imaging apparatus according to the aspect of the present invention, the imaging interval setting portion may acquire the number of cells on the basis of a shape of a cell included in each of the first biological sample and the second biological sample.

In the imaging apparatus according to the aspect of the present invention, the imaging interval setting portion may acquire, as the feature data, the number of dead cells among cells included in each of the first biological sample and the second biological sample.

In the imaging apparatus according to the aspect of the present invention, the imaging interval setting portion may acquire the number of dead cells on the basis of a shape of a dead cell included in each of the first biological sample and the second biological sample.

In the imaging apparatus according to the aspect of the present invention, the imaging interval setting portion may acquire, as the feature data, feature data of a shape of a cell included in each of the first biological sample and the second biological sample.

In the imaging apparatus according to the aspect of the present invention, the imaging interval setting portion may acquire, as the feature data, an area of a cell included in each of the first biological sample and the second biological sample.

In the imaging apparatus according to the aspect of the present invention, the imaging interval setting portion may acquire, as the feature data, at least one of feature data of shapes, the number, feature data of a spatial distribution, or a density of organelles of a cell included in each of the first biological sample and the second biological sample.

In the imaging apparatus according to the aspect of the present invention, the imaging interval setting portion may acquire, as the feature data, at least one of feature data of shapes, the number, feature data of a spatial distribution, or a density of cell nucleuses, nucleoli, or mitochondria.

In the imaging apparatus according to the aspect of the present invention, the cell may be a pluripotent stem cell.

In the imaging apparatus according to the aspect of the present invention, the imaging interval setting portion may acquire, as the feature data, an intensity of light emitted from the first biological sample and the second biological sample or feature data of a spatial distribution of emitted light.

In the imaging apparatus according to the aspect of the present invention, at least one of the first process or the second process is preferably a process of adding a compound.

In the imaging apparatus according to the aspect of the present invention, preferably, the first process is a process of adding a compound, and the second process is a process of not adding the compound.

The imaging apparatus according to the aspect of the present invention may further comprise a processing unit that performs the first process and the second process.

In the imaging apparatus according to the aspect of the present invention, the imaging unit preferably includes a microscope.

According to another aspect of the present invention, there is provided an imaging method comprising imaging, in a time series order, each of a first biological sample having undergone a first process and a second biological sample which has undergone a second process which is a comparison target with the first process, is different from the first process and is of the same type as the type of the first biological sample; acquiring a first image obtained by imaging the first biological sample, and a second image obtained by imaging the second biological sample at the same timing as a timing of the first image, and setting an imaging interval of the first biological sample and the second biological sample on the basis of a difference between feature data of the first image and feature data of the second image or a change amount of the difference; and imaging the first biological sample and the second biological sample by using the set imaging interval.

According to the imaging apparatus and the imaging method according to the aspects of the present invention, each of a first biological sample having undergone a first process and a second biological sample which has undergone a second process which is different from the first process is imaged in a time series order, and a first image obtained by imaging the first biological sample, and a second image obtained by imaging the second biological sample at the same timing as a timing of the first biological sample are acquired.

An imaging interval of the first biological sample and the second biological sample is set on the basis of a difference between feature data of the first image and feature data of the second image or a change amount of the difference, and the first biological sample and the second biological sample are imaged by using the set imaging interval.

As mentioned above, the difference between the feature data of the first image and the feature data of the second image or the change amount of the difference is acquired, and thus it is possible to cancel out a change in feature data due to an environment in which the biological sample is placed or the like.

Since an imaging interval is set on the basis of a difference between the feature data of the first image and the feature data of the second image or a change amount of the difference, an imaging interval of a biological sample can be appropriately set, and thus it is possible to capture an image in which a temporal change of a state of the biological sample is checked in more detail without performing wasteful imaging.

BRIEF DESCRIPTION OF THE DRAWINGS

FIGS. 6A and 6B are diagrams illustrating an example of a change of the number of cells in a case where different types of anticancer drugs are respectively added to a first biological sample and a second biological sample.

FIG. 7 is a diagram illustrating an example of a temporal change of a difference between the number of cells of the first biological sample and the number of cells of the second biological sample in a case where the different types of anticancer drugs are respectively added to the first biological sample and the second biological sample.

DESCRIPTION OF THE PREFERRED EMBODIMENTS

Figure 1:
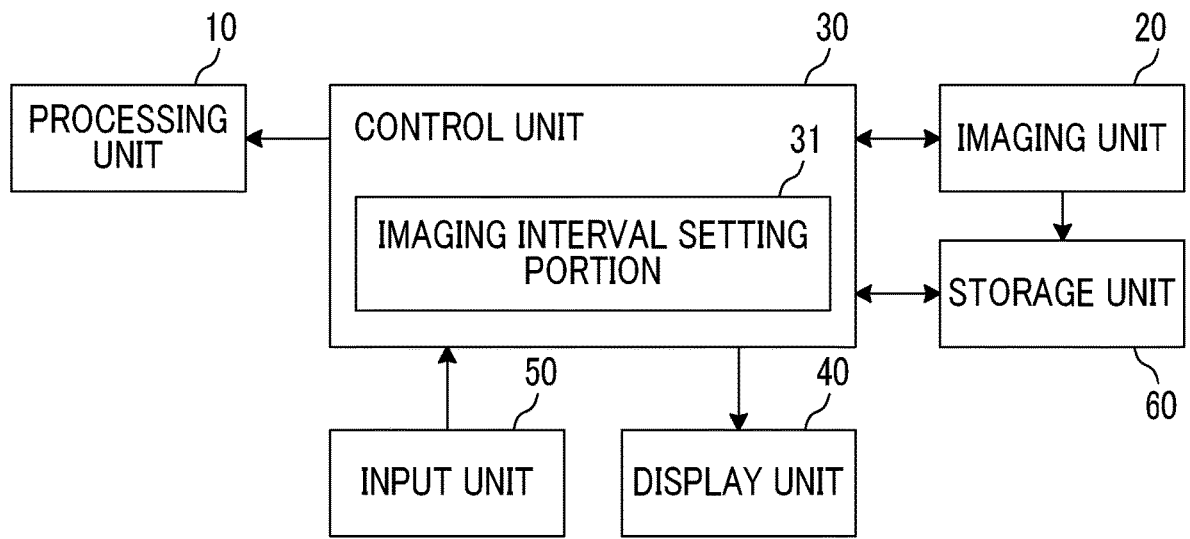
FIG. 1 is a block diagram illustrating a schematic configuration of a biological sample imaging system using an imaging apparatus according to an embodiment of the present invention.

Hereinafter, with reference to the drawings, a biological sample imaging system using an imaging apparatus and an imaging method according to an embodiment of the present invention will be described in detail. FIG. 1 is a block diagram illustrating a schematic configuration of the biological sample imaging system of the present embodiment.

The biological sample imaging system of the present embodiment comprises, as illustrated in FIG. 1, a processing unit 10, an imaging unit 20, a control unit 30, a display unit 40, an input unit 50, and a storage unit 60. In the present embodiment, the processing unit 10, the imaging unit 20, and the control unit 30 configure an imaging apparatus according to an embodiment of the present invention.

First, in a case where biological samples are imaged in the biological sample imaging system of the present embodiment, an identical type of a first biological sample and a second biological sample are prepared. For example, in a case where a biological sample is a cell, the identical type of biological samples are cultured from a single cell strain, and the first biological sample and the second biological sample are created by dispensing the single cell strain to an identical type of two or more containers in an identical amount. In other words, the first biological sample and the second biological sample are a cell group regarded to be substantially identical in evaluation of a state change of the cell group.

Examples of biological samples include pluripotent stem cells such as cancer cells, induced pluripotent stem cells (iPS), and embryonic stem cells (ES), cells of a nerve, skin, cardiac muscle, or liver differentiated and induced from a stem cell, or cells of skin, a retina, cardiac muscle, a blood corpuscle, a nerve, or an organ extracted from a human body.

In the present embodiment, a description will be made of an example in which cancer cells are prepared as the first biological sample and the second biological sample, and an effect of an anticancer drug is evaluated. In other words, the first biological sample and the second biological sample are created by dispensing the cancer cells to two containers of an identical type in an identical amount. As a container, for example, a petri dish may be used, a multi-well plate may be used, and different wells of a single multi-well plate may be used.

Creation of the first biological sample and the second biological sample may be manually performed by a user, and may be automatically performed by using, for example, an apparatus configured with a mechanism sucking cells, a robot arm, and the like.

The processing unit 10 performs a first process on the first biological sample created as described above, and performs a second process on the second biological sample. Specifically, the processing unit 10 performs the first process by adding, to the first biological sample, a solution in which an evaluation target anticancer drug is dissolved in a solvent. On the other hand, the second process is performed by adding only the solvent to the second biological sample in the same amount as an amount of the added solvent in the first process. The processing unit 10 performs the first process and the second process by using, for example, an automatic dispensing device. The first process and the second process are performed at an identical timing, but there may be a difference to the extent of not influencing evaluation of an effect of the anticancer drug. In the present embodiment, the anticancer drug corresponds to a compound in the present invention.

The first process on the first biological sample and the second process on the second biological sample may be manually performed by a user.

The imaging unit 20 images the first biological sample having undergone the first process and the second biological sample having undergone the second process in a time series order a plurality of times. In other words, the imaging unit 20 performs time-lapse imaging of the first biological sample and the second biological sample.

Specifically, the imaging unit 20 comprises, for example, a phase difference microscope, a differential interference microscope, a bright-field microscope, or a fluorescence microscope. Such a microscope comprises an imaging element such as a complementary metal-oxide semiconductor (CMOS) sensor or a charge-coupled device (CCD) sensor.

The imaging unit 20 images the first biological sample and the second biological sample at an identical timing, so as to acquire a first image of the first biological sample and a second image of the second biological sample. Here, the identical timing may not necessarily be an exactly identical timing, and there may be a difference to the extent of not influencing evaluation of an effect of the anticancer drug.

An interval at which each of the first biological sample and the second biological sample is imaged by the imaging unit 20 is set by an imaging interval setting portion 31 which will be described later. A method of setting an imaging interval will be described later in detail. An initial value of an imaging interval may be set by a user, and the imaging interval is set according to the purpose of evaluation.

A first image and a second image captured by the imaging unit 20 are sequentially output to and stored in the storage unit 60.

A well-known conveyance mechanism such as a conveyer belt, a turn table, or a robot arm may be used to move the first biological sample and the second biological sample from the processing unit 10 to the imaging unit 20.

The control unit 30 is configured with a central processing unit (CPU), a semiconductor memory, and the like. The control unit 30 controls the entire biological sample imaging system, and, particularly, the control unit 30 of the present embodiment comprises the imaging interval setting portion 31. The control unit 30 and the storage unit 60 may be configured with a single computer.

The imaging interval setting portion 31 receives images which are captured by the imaging unit 20 in a time series order, and sets imaging intervals of the first biological sample and the second biological sample on the basis of feature data of the received images. Since the first biological sample and the second biological sample are imaged at an identical timing, an imaging interval of the first biological sample and the second biological sample will be simply referred to as an imaging interval without specifying an imaging target.

Specifically, the imaging interval setting portion 31 acquires feature data of the first image obtained by imaging the first biological sample and feature data of the second image obtained by imaging the second biological sample at the same timing as that of the first image, and sets an imaging interval on the basis of a difference between the feature data of the first image and the feature data of the second image or a change amount of the difference.

In the present embodiment, the imaging interval setting portion 31 acquires the number of cells included in the first biological sample as the feature data of the first image, and acquires the number of cells included in the second biological sample as the feature data of the second image.

Regarding a method of acquiring the number of cells from the first image and the second image, for example, there may be a method in which a shape of the cell is set in advance, an image of the cell included in the first image and the second image is specified through an imaging process such as pattern matching, and the number of cells is acquired by counting the number of images of the cell. However, a method of acquiring the number of cells is not limited thereto, and various well-known processes may be used.

The imaging interval setting portion 31 calculates an absolute value of a difference between the number of cells included in the first image and the number of cells included in the second image, and sets an imaging interval according to the magnitude of the absolute value the difference.

Here, as in the present embodiment, in a case where an anticancer drug is added to the first biological sample, and the anticancer drug is not added to the second biological sample, the number of cells of the first biological sample is typically gradually reduced. On the other hand, the anticancer drug is not added to the second biological sample, and thus the number of cells is not reduced.

However, the number of cells may be reduced due to factors other than the effect of the anticancer drug, caused by an environment in which the first biological sample and the second biological sample are placed and weak viability of the first biological sample and the second biological sample. The reduction of the number of cells occurs in both of the first biological sample to which the anticancer drug is added and the second biological sample to which the anticancer drug is not added.

Therefore, as described above, an absolute value of a difference between the number of cells included in the first image and the number of cells included in the second image is calculated, and thus it is possible to cancel out the number of reduced cells caused by an environment in which the biological sample is placed or the like. In other words, it is possible to acquire only the number of reduced cells due to the effect of the anticancer drug added to the first biological sample.

Figure 2:
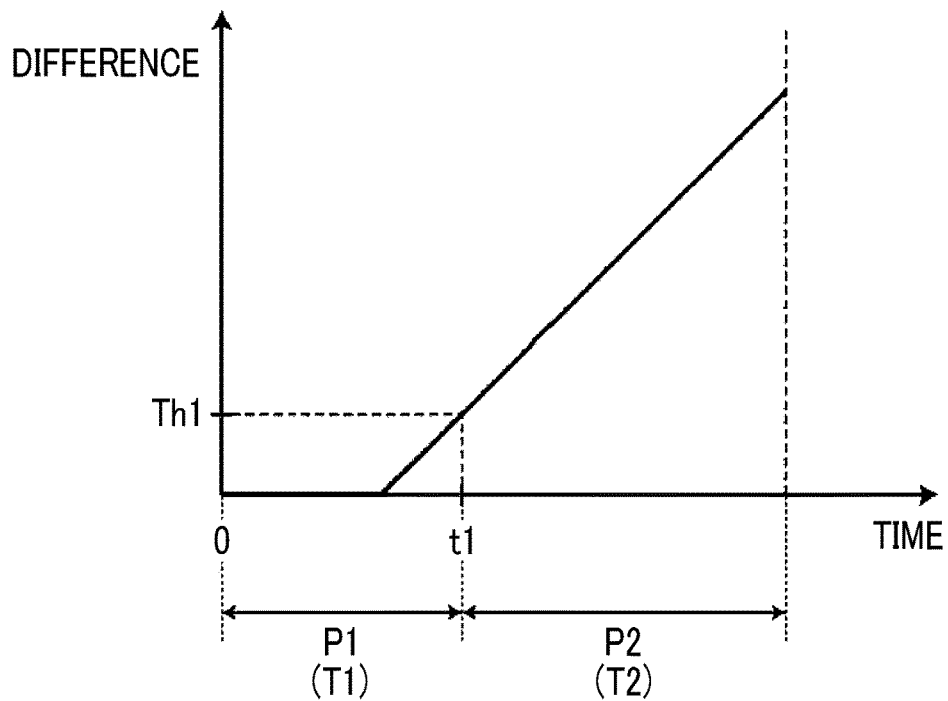
FIG. 2 is a diagram illustrating an example of a temporal change of an absolute value of a difference between the number of cells in a first image and the number of cells in a second image.

FIG. 2 illustrates an example of a temporal change of an absolute value of a difference between the number of cells in the first image and the number of cells in the second image. In a case where there is an effect of the anticancer drug, the number of cells in the first image is reduced, and thus a difference between the number of cells in the first image and the number of cells in the second image gradually increases over time as illustrated in FIG. 2, for example.

Here, a state of the first biological sample greatly changes during a period in which the effect of the anticancer drug appears, and thus it is important to analyze images captured in this period in detail. Therefore, the imaging interval setting portion 31 of the present embodiment performs imaging by using an imaging interval T1 which is an initial value in a period P1 from imaging starting to a time point t1, and changes an imaging interval to an imaging interval T2 shorter than the imaging interval T1, and continuously performs imaging, in a case where an absolute value of a difference between feature data of the first image and feature data of the second image is equal to or greater than a preset first threshold value Th1, that is, in a period P2 after the time point t1.

An imaging interval is changed to be short in a case where an absolute value of a difference in feature data is equal to or greater than the first threshold value Th1, and thus more images can be captured, so that a state change of the first biological sample can be analyzed in more detail.

The imaging interval T2 may be changed according to the magnitude of an absolute value of a difference. Specifically, as an absolute value of a difference becomes greater, the imaging interval T2 may be set to become shorter, and, as an absolute value of a difference becomes smaller, the imaging interval T2 may be set to become longer. In this case, a function of the imaging interval T2 having an absolute value of a difference as a variable may be set in advance.

The first threshold value may be set in multiple stages, that is, the first threshold value having a plurality of magnitudes may be set, and the imaging interval T2 may be adjusted in multiple stages. The imaging interval T2 may be set to be short whenever an absolute value of a difference exceeds the first threshold value set in multiple stages.

The control unit 30 controls an imaging operation of the imaging unit 20 on the basis of an imaging interval set by the imaging interval setting portion 31.

The display unit 40 comprises a display device such as a liquid crystal display. The display unit 40 displays an image or the like captured by the imaging unit 20. As described above, in a case where an imaging interval is changed by the imaging interval setting portion 31, the information indicating the change may be displayed on the display unit 40.

The input unit 50 comprises an input device such as a keyboard or a mouse, and receives various setting inputs from a user. For example, a setting input of an initial value of an imaging interval of the imaging unit 20 is received.

The storage unit 60 comprises a storage device such as a semiconductor memory, a hard disk, or a solid state drive (SSD). As described above, the control unit 30 and the storage unit 60 may be configured with a single computer, and the control unit 30 may be configured with a single computer, and the storage unit 60 may be provided separately from the computer.

Figure 3:
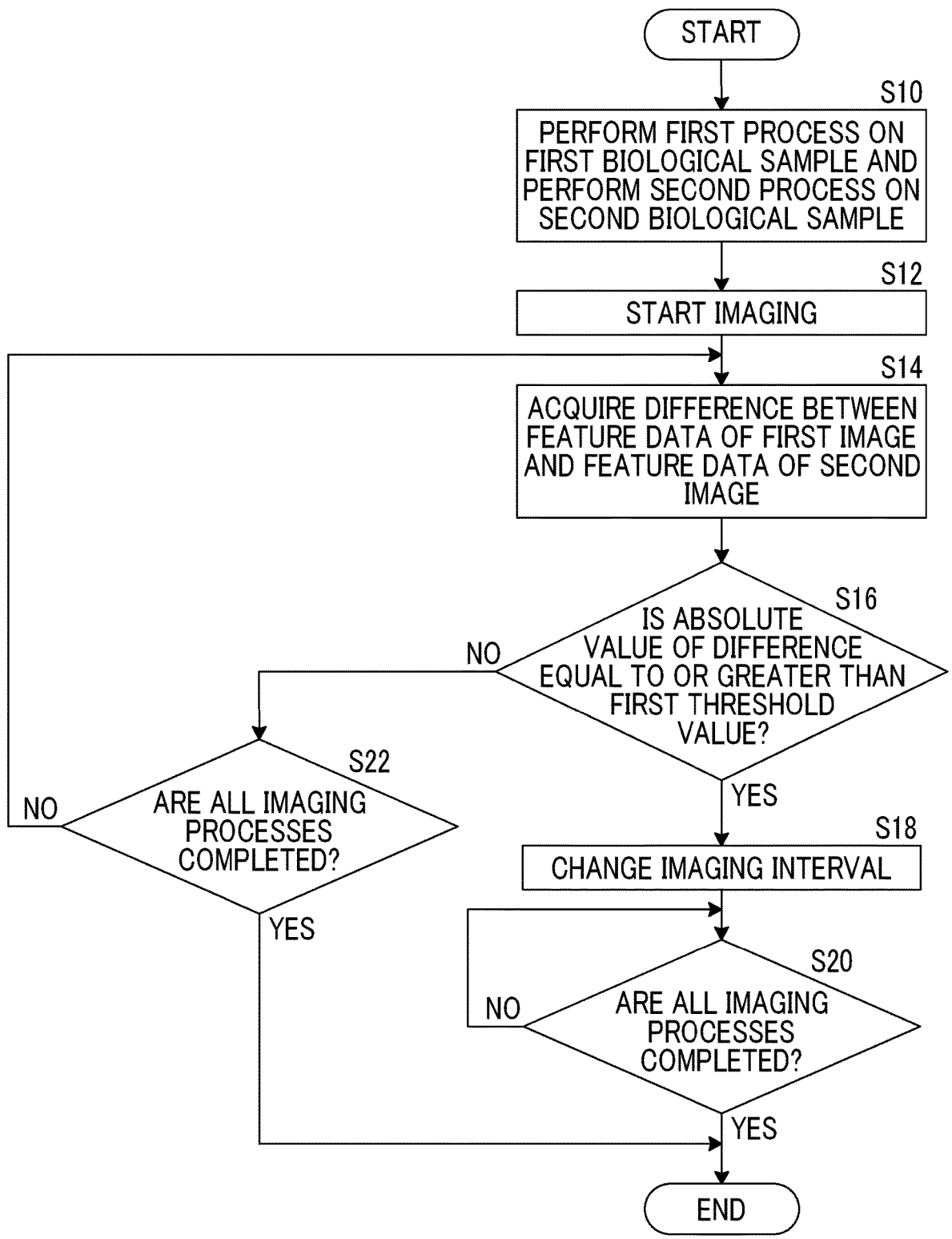
FIG. 3 is a flowchart for explaining an operation of the biological sample imaging system using the imaging apparatus according to the embodiment of the present invention.

Next, a description will be made of an operation of the biological sample imaging system of the present embodiment with reference to a flowchart in FIG. 3.

First, the first biological sample and the second biological sample are created and are provided in the processing unit 10. The processing unit 10 adds a solvent containing an anticancer drug to the first biological sample so as to perform the first process. Only the solvent is added to the second biological sample, and thus the second process is performed (S10).

Next, the first biological sample having undergone the first process and the second biological sample having undergone the second process are provided in the imaging unit 20. The imaging unit 20 starts to perform imaging, and images the first biological sample and the second biological sample at an identical timing in a time series order (S12). An imaging interval at this time is set to an initial value.

The first image of the first biological sample and the second image of the second biological sample captured by the imaging unit 20 are sequentially output to and stored in the storage unit 60. The imaging interval setting portion 31 reads the first image and the second image stored in the storage unit 60, and calculates feature data of each of the first image and the second image captured at an identical timing. In the present embodiment, as described above, the number of cancer cells included in the first image and the number of cancer cells included in the second image are calculated as the feature data.

Next, the imaging interval setting portion 31 calculates a difference between the feature data of the first image and the feature data of the second image (S14), and determines whether or not an absolute value thereof is equal to or greater than the first threshold value Th1. In a case where the absolute value of the difference is equal to or greater than the first threshold value Th1 (YES in S16), the imaging interval setting portion 31 changes an imaging interval. Specifically, the imaging interval is changed to an imaging interval shorter than the imaging interval corresponding to the initial value (S18).

The control unit 30 controls the imaging unit 20 on the basis of the changed imaging interval, and the imaging unit 20 continuously images the first biological sample and the second biological sample by using the imaging interval shorter than the initial value.

In a case where a preset imaging period has elapsed, the control unit 30 finishes the imaging process (YES in S20).

On the other hand, in a case where the absolute value of the difference between the feature data of the first image and the feature data of the second image is smaller than the first threshold value Th1 in S16 (NO in S16), the control unit 30 continuously images the first biological sample and the second biological sample at the imaging interval corresponding to the initial value without changing the imaging interval. The control unit 30 sequentially calculates a difference between feature data of the first image and feature data of the second image as described above until the preset imaging period elapses, and repeatedly determines whether or not an absolute value of the difference is equal to or greater than the first threshold value Th1 (NO in S22). On the other hand, in a case where imaging is continuously performed at the imaging interval corresponding to the initial value, and the preset imaging period elapses, the control unit 30 finishes the imaging process (YES in S22).

In the present embodiment, a description has been made of a case where an imaging interval is changed on the basis of a difference between feature data of the first image of the first biological sample and feature data of the second image of the second biological sample, but an imaging interval may be changed on the basis of a difference change amount. For example, in a case where an absolute value of a difference between feature data of the first image and feature data of the second image linearly increases as illustrated in FIG. 2, a difference change amount shows a change as illustrated in FIG. 4.

Therefore, imaging may be performed by using the imaging interval T1 which is an initial value in the period P1, and an imaging interval may be changed to the imaging interval T2 shorter than the imaging interval T1 in a case where a change amount of a difference between feature data of the first image and feature data of the second image is equal to or greater than a preset first threshold value Th2, that is, in the period P2 after the time point t1.

Figure 4:
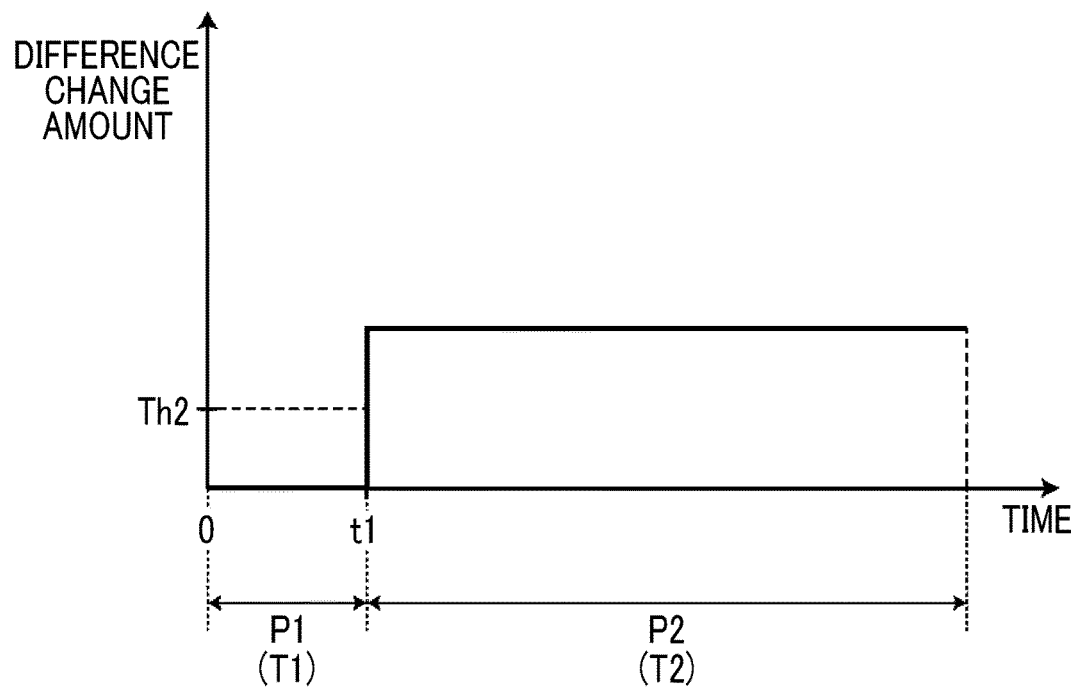
FIG. 4 is a diagram illustrating an example of a temporal change of a change amount of a difference between the number of cells in the first image and the number of cells in the second image.

A change amount of a difference between feature data of the first image and feature data of the second image is not necessarily limited to the change as illustrated in FIG. 4. There is a case where cancer cells of the first biological sample are reduced in a nonlinear manner, for example, the cancer cells are rapidly reduced, then gently reduced, and are settled down to a constant number. In this case, a change amount of a difference between feature data of the first image and feature data of the second image shows a change as illustrated in FIG. 5.

Figure 5:
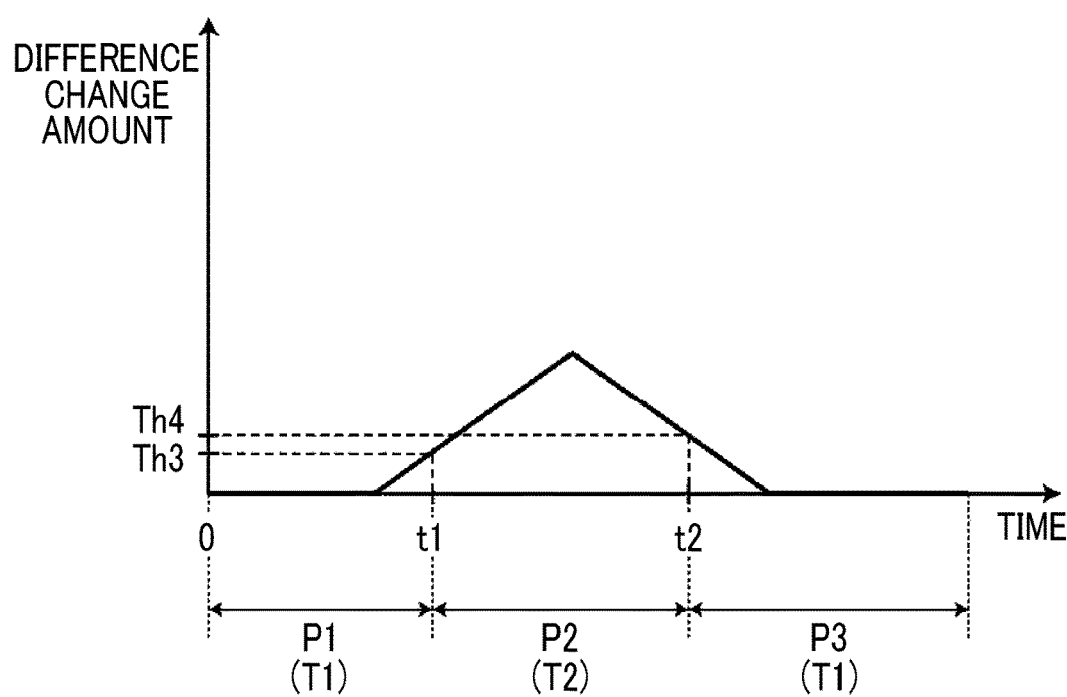
FIG. 5 is a diagram illustrating another example of a temporal change of a change amount of a difference between feature data of the first image and feature data of the second image.

In a case where a change amount of a difference in feature data changes as illustrated in FIG. 5, imaging may be performed by using the imaging interval T1 which is an initial value in the period P1 from imaging starting to the time point t1, and the first image and the second image may be continuously captured by changing an imaging interval to the imaging interval T2 shorter than the imaging interval T1 in the period P2 after the time point t1 at which the change amount of the difference in the feature data is equal to or greater than a preset first threshold value Th3. The first image and the second image may be continuously captured by returning an imaging interval to the imaging interval T1 in a period P3 after a time point t2 at which the change amount of the difference in the feature data is equal to or smaller than a preset second threshold value Th4.

By changing an imaging interval as mentioned above, more images can be captured in a period in which a state change of the first biological sample is great, and thus it is possible to analyze the state change of the first biological sample in more detail. In a period in which a state change of the first biological sample is gradually settled, an imaging period is lengthened again, and thus capturing of a wasteful image can be reduced, so that a storage capacity of the storage unit 60 can be saved.

A relationship between magnitudes of the first threshold value Th3 and the second threshold value Th4 is not particularly limited, may be Th3=Th4, may be Th3>Th4, and may be Th3<Th4.

The imaging interval T2 may be changed according to the magnitude of a difference change amount. Specifically, as a difference change amount becomes larger, the imaging interval T2 may be set to become shorter, and, a difference change amount becomes smaller, the imaging interval T2 may be set to become longer. In this case, a function of the imaging interval T2 having a difference change amount as a variable may be set in advance.

In the present embodiment, in order to evaluate an effect of an anticancer drug, the anticancer drug is added to the first biological sample, and the anticancer drug is not added to the second biological sample, but the purpose of evaluation is not limited thereto, and a difference between effects of two types of anticancer drugs may be desired to be evaluated through comparison. Also in this case, evaluation using the biological sample imaging system of the present embodiment is preferably performed.

Specifically, for example, a first process is performed by adding a first anticancer drug to the first biological sample, and a second process is performed by adding a second anticancer drug which is a comparison target to the second biological sample. In the same manner as in the embodiment, a first image of the first biological sample and a second image of the second biological sample are sequentially imaged in a time series order, and a difference between feature data of the first image and feature data of the second image is sequentially calculated.

Here, for example, in a case where an effect of the first anticancer drug appears faster than an effect of the second anticancer drug, the number of cells of the first biological sample to which the first anticancer drug is added is reduced as in FIG. 6A, and the number of cells of the second biological sample to which the second anticancer drug is added is reduced as in FIG. 6B.

In a case where the number of cells of the first and second biological samples is reduced as in FIGS. 6A and 6B, a difference between feature data (number of cells) of the first image and feature data (number of cells) of the second image changes as illustrated in FIG. 7.

In a case where a difference in feature data changes as illustrated in FIG. 7, imaging may be performed by using the imaging interval T1 which is an initial value in the period P1 from imaging starting to the time point t1, and the first image and the second image may be continuously captured by changing an imaging interval to the imaging interval T2 shorter than the imaging interval T1 in the period P2 after a time point t1_2 at which the difference in the feature data is equal to or more than a preset first threshold value Th5. The first image and the second image may be continuously captured by returning an imaging interval to the imaging interval T1 in a period P3 after a time point t3_4 at which the difference is equal to or less than a preset second threshold value Th6.

By changing an imaging interval as mentioned above, more images can be captured in a period in which a state change of the first biological sample or the second biological sample is great, and thus it is possible to analyze the state change of the first biological sample or the second biological sample in more detail. In a period in which state changes of the first biological sample and the second biological sample are gradually settled, an imaging period is lengthened again, and thus capturing of a wasteful image can be reduced, so that a storage capacity of the storage unit 60 can be saved.

A relationship between magnitudes of the first threshold value Th5 and the second threshold value Th6 is not particularly limited, may be Th5=Th6, may be Th5>Th6, and may be Th5<Th6.

In the present embodiment, the number of cancer cells is acquired as feature data of the first image and the second image, but feature data is not limited thereto. For example, as feature data, the number of dead cells included in the first biological sample and the second biological sample may be acquired. Regarding a method of acquiring the number of dead cells, for example, there may be a method in which a shape of the dead cell is set in advance, an image of the dead cell included in the first image and the second image is specified through an imaging process such as pattern matching, and the number of dead cells is acquired by counting the number of images of the dead cell.

As feature data of the first image and the second image, feature data based on a shape of a cell included in the first biological sample and the second biological sample may be acquired. The feature data based on a shape of a cell includes, for example, an average value of diameters or lengths of a plurality of cells included in the first image and the second image, or an average value of circularities of a plurality of cells included in the first image and the second image.

As feature data of the first image and the second image, feature data based on an area of a cell included in the first biological sample and the second biological sample may be acquired. As the feature data based on an area of a cell, for example, an average value of areas of a plurality of cells included in the first image and the second image may be acquired, and a total area value obtained by adding areas of a plurality of cells together may be acquired.

Cells of the first biological sample and cells of the second biological sample may be labeled with fluorescence, and the intensity of the fluorescence or feature data of a spatial distribution of the fluorescence may be acquired as feature data of the first image and the second image. For example, a distribution of spatial frequencies of fluorescent portions included in the first image and the second image may be acquired as the feature data of a spatial distribution of the fluorescence.

As feature data of the first image and the second image, feature data based on a cell organelle included in the first biological sample and the second biological sample may be acquired. The cell organelle includes a cell nucleus, a nucleolus, or a mitochondria. The feature data based on a cell organelle includes feature data of shapes, the number, feature data of a spatial distribution, or a density of cell organelles. For example, a cancer cell has a larger cell nucleus than a normal cell or has a non-uniform shape of the cell nucleus. Therefore, for example, the number of cell nucleuses having a preset size or more may be acquired as feature data of a shape of a cell organelle, or the uniformity of a shape of a cell nucleus may be acquired as the feature data. Regarding the feature data of a spatial distribution of cell organelles, for example, power spectra of spatial frequencies of the first image and the second image may be calculated, and a peak thereof may be acquired as the feature data.

In the embodiment, a description has been made of a case where an effect of an anticancer drug is evaluated, but this is only an example. For example, pluripotent stem cells may be used as the first biological sample and the second biological sample, the first process may be performed by adding a solvent containing a growth factor a feeder cell to the first biological sample, and the second process may be performed by adding only the solvent to the second biological sample. Consequently, it is possible to evaluate an effect of the growth factor or the feeder cell.

The growth of the pluripotent stem cell is influenced not only by a growth factor or a feeder cell but also by a culture environment of the pluripotent stem cell and the activity of the pluripotent stem cell. Therefore, as described above, the first biological sample to which the growth factor or the feeder cell is added and the second biological sample to which the growth factor or the feeder cell is not added is imaged, and a difference between feature data of the first image of the first biological sample and feature data of the second image of the second biological sample is acquired such that only a change in the growth due to the growth factor or the feeder cell can be acquired. As the feature data of the first and second images in this case, for example, the number of pluripotent stem cells, feature data of a shape thereof, or an area thereof may be used as described above.

In the growth process of the pluripotent stem cell, a distribution state of nucleoli of the pluripotent stem cell changes. Specifically, in a case where the pluripotent stem cell is maintained in a non-differentiation state, nucleoli are spatially densely distributed, and, in a case where differentiation of the pluripotent stem cell is in progress, the nucleoli are roughly distributed. Therefore, the density of nucleoli may be acquired as the feature data of the first image and the second image.

As the first biological sample and the second biological sample, as described above, cells differentiated and induced from a pluripotent stem cell may be used, and, for example, differentiated and induced nerve cells may be used. Also in this case, a solvent containing a growth factor or a feeder cell may be added as the first process, and only the solvent may be added as the second process. In this case, for example, a length of a dendrite of the nerve cell may be calculated as feature data of the first image and the second image.

EXPLANATION OF REFERENCES

10: processing unit
20: imaging unit
30: control unit
31: imaging interval setting portion
40: display unit
50: input unit
60: storage unit

What is claimed is:

1. An imaging apparatus comprising:
an imaging sensor configured to image, in a time series order, each of a first biological sample having undergone a first process and a second biological sample which has undergone a second process which is a comparison target with the first process, is different from the first process, and is of the same type as the type of the first biological sample; and
a processor configured to acquire a first image obtained by imaging the first biological sample, and a second image obtained by imaging the second biological sample at the same timing as a timing of the first image, and to set an imaging interval of the first biological sample and the second biological sample on the basis of a difference between feature data of the first image and feature data of the second image or a change amount of the difference,
wherein the imaging sensor is further configured to image the first biological sample and the second biological sample by using the imaging interval set by the processor.

2. The imaging apparatus according to claim 1,
wherein the processor is further configured to set an imaging interval after an imaging time point of the first image and the second image to be shorter than an imaging interval related to the imaging time point in a case where a difference between the feature data of the first image and the feature data of the second image or a change amount of the difference is equal to or more than a preset first threshold value.

3. The imaging apparatus according to claim 1,
wherein the processor is further configured to set an imaging interval after an imaging time point of the first image and the second image to be longer than an imaging interval related to the imaging time point in a case where a difference between the feature data of the first image and the feature data of the second image or a change amount of the difference is equal to or less than a preset second threshold value.

4. The imaging apparatus according to claim 1,
wherein the processor is further configured to set the imaging interval to become shorter as a difference between the feature data of the first image and the feature data of the second image or a change amount of the difference becomes larger.

5. The imaging apparatus according to claim 1,
wherein the processor is further configured to set the imaging interval to become longer as a difference between the feature data of the first image and the feature data of the second image or a change amount of the difference becomes smaller.

6. The imaging apparatus according to claim 1,
wherein the processor is further configured to acquire, as the feature data, the number of cells included in each of the first biological sample and the second biological sample.

7. The imaging apparatus according to claim 6,
wherein the processor is further configured to acquire the number of cells on the basis of a shape of a cell included in each of the first biological sample and the second biological sample.

8. The imaging apparatus according to claim 1,
wherein the processor is further configured to acquire, as the feature data, the number of dead cells among cells included in each of the first biological sample and the second biological sample.

9. The imaging apparatus according to claim 8,
wherein the processor is further configured to acquire the number of dead cells on the basis of a shape of a dead cell included in each of the first biological sample and the second biological sample.

10. The imaging apparatus according to claim 1,
wherein the processor is further configured to acquire, as the feature data, feature data of a shape of a cell included in each of the first biological sample and the second biological sample.

11. The imaging apparatus according to claim 1,
wherein the processor is further configured to acquire, as the feature data, an area of a cell included in each of the first biological sample and the second biological sample.

12. The imaging apparatus according to claim 1,
wherein the processor is further configured to acquire, as the feature data, at least one of feature data of shapes, a number, feature data of a spatial distribution, or a density of organelles of a cell included in each of the first biological sample and the second biological sample.

13. The imaging apparatus according to claim 12,
wherein the processor is further configured to acquire, as the feature data, at least one of feature data of shapes, the number, feature data of a spatial distribution, or a density of cell nucleuses, nucleoli, or mitochondria.

14. The imaging apparatus according to claim 6,
wherein the cell is a pluripotent stem cell.

15. The imaging apparatus according to claim 1,
wherein the processor is further configured to acquire, as the feature data, an intensity of light emitted from the first biological sample and the second biological sample or feature data of a spatial distribution of emitted light.

16. The imaging apparatus according to claim 1,
wherein at least one of the first process or the second process is a process of adding a compound.

17. The imaging apparatus according to claim 16,
wherein the first process is a process of adding a compound, and the second process is a process of not adding the compound.

18. The imaging apparatus according to claim 1, further comprising:
a processing unit that performs the first process and the second process.

19. The imaging apparatus according to claim 1,
wherein the imaging sensor includes a microscope.

20. An imaging method comprising:
imaging, in a time series order, each of a first biological sample having undergone a first process and a second biological sample which has undergone a second process which is a comparison target with the first process, is different from the first process and is of the same type as the type of the first biological sample;
acquiring a first image obtained by imaging the first biological sample, and a second image obtained by imaging the second biological sample at the same timing as a timing of the first image, and setting an imaging interval of the first biological sample and the second biological sample on the basis of a difference between feature data of the first image and feature data of the second image or a change amount of the difference; and imaging the first biological sample and the second biological sample by using the set imaging interval.

* * * * *